United States Patent [19]

Thomas et al.

[11] 4,063,556
[45] Dec. 20, 1977

[54] VACUUM CURETTAGE DEVICE

[75] Inventors: Michael D. Thomas, Arab, Ala.; Francis E. Ryder, Barrington, Ill.

[73] Assignee: Ryder International Corporation, Schaumberg, Ill.

[21] Appl. No.: 676,759

[22] Filed: Apr. 14, 1976

[51] Int. Cl.² .................. A61M 1/00; A61B 17/22; G01D 13/00; F16K 1/20
[52] U.S. Cl. .................. 128/276; 116/114 PV; 251/302
[58] Field of Search .............. 116/114 C, 114 PV; 128/276; 251/302, 304

[56] References Cited

U.S. PATENT DOCUMENTS

| | | | |
|---|---|---|---|
| 1,798,952 | 3/1931 | Pellegrino | 251/302 X |
| 2,781,787 | 2/1957 | Johnson | 251/302 X |
| 2,913,220 | 11/1959 | Cover | 251/302 X |
| 3,334,628 | 8/1967 | Saemann et al. | 116/114 PV X |
| 3,833,000 | 9/1974 | Bridgman | 128/276 |
| 3,843,016 | 10/1974 | Bornhorst et al. | 128/276 X |
| 3,946,739 | 3/1976 | Berman et al. | 128/276 X |
| 3,963,891 | 6/1976 | de Magondeaux | 116/114 PV X |

Primary Examiner—Channing L. Pace
Attorney, Agent, or Firm—Olson, Trexler, Wolters, Bushnell & Fosse, Ltd.

[57] ABSTRACT

A vacuum device for performing medical procedures such as a curettage, or the like. The device includes basically an evacuated vessel, a cannula or some other form of medical implement, and a valve arrangement for selectively applying the vacuum to the cannula. The present disclosure deals specifically with a novel valve arrangement for the device and various vacuum indicators that can be employed to provide a visual indication as to the presence of a vacuum within the vessel.

12 Claims, 13 Drawing Figures

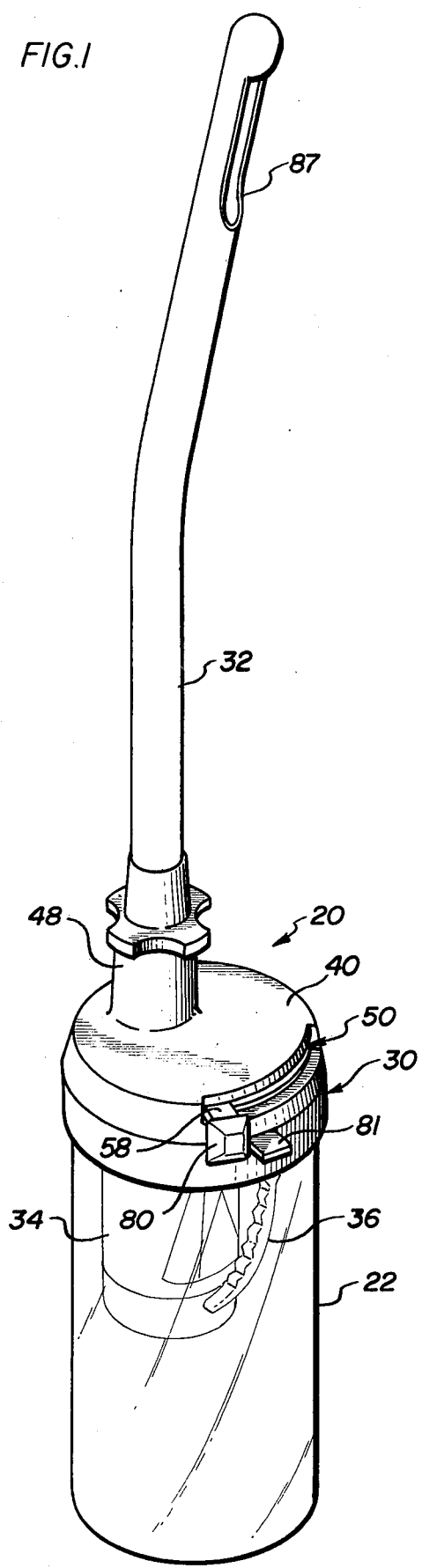
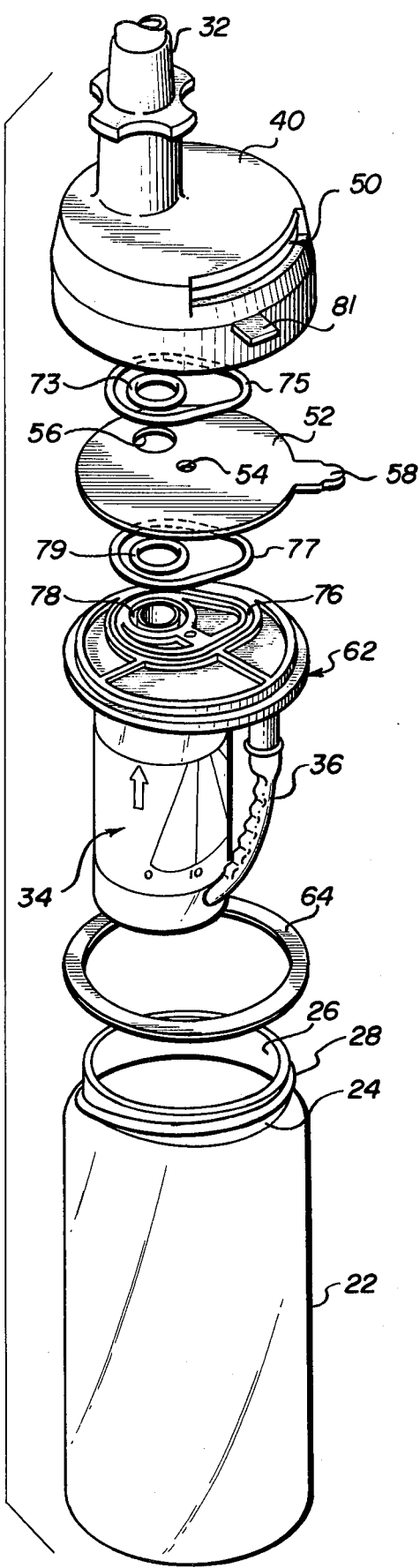

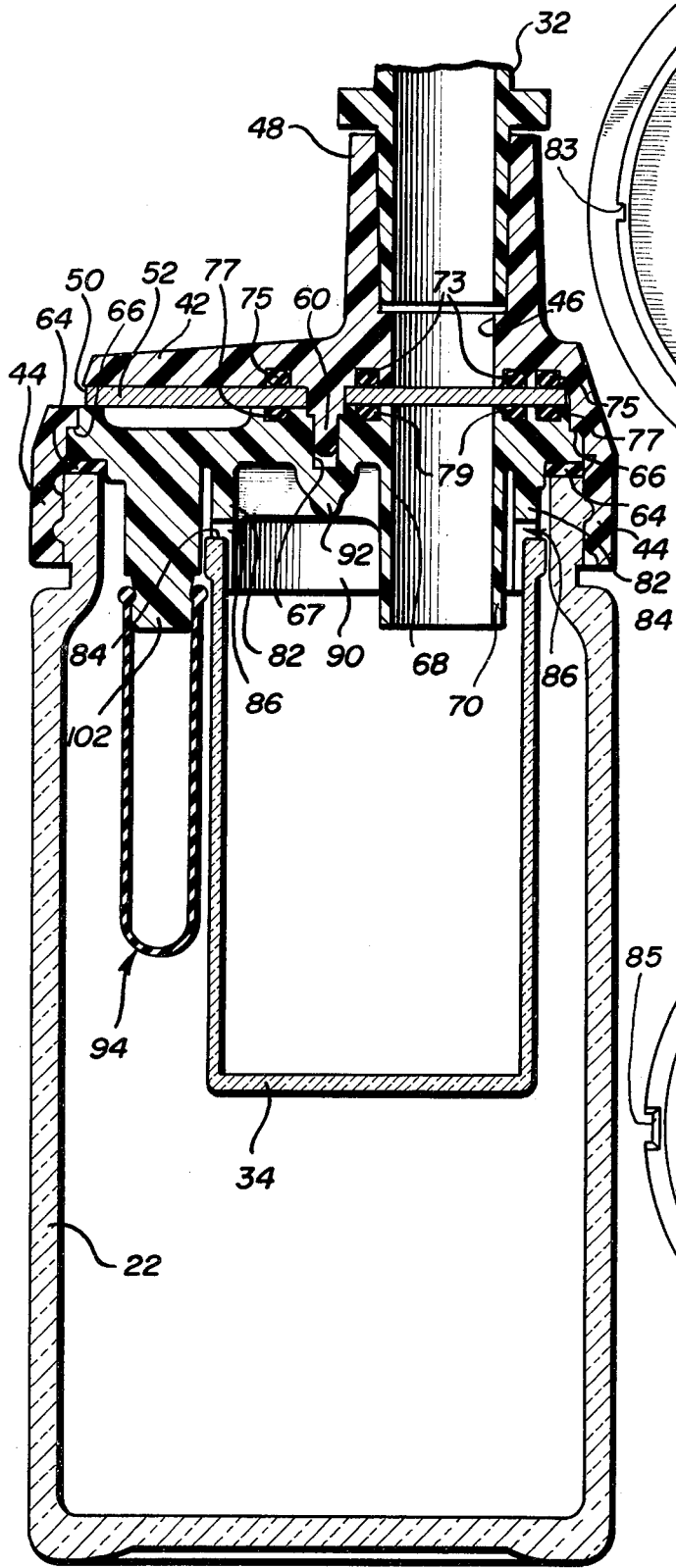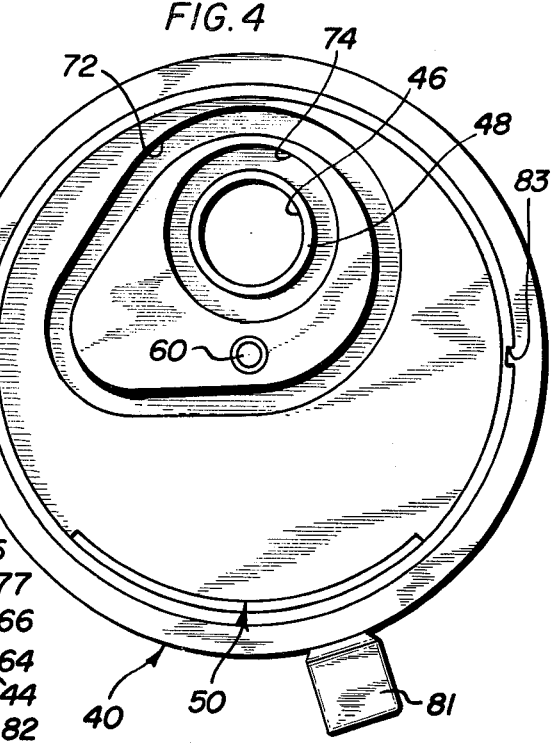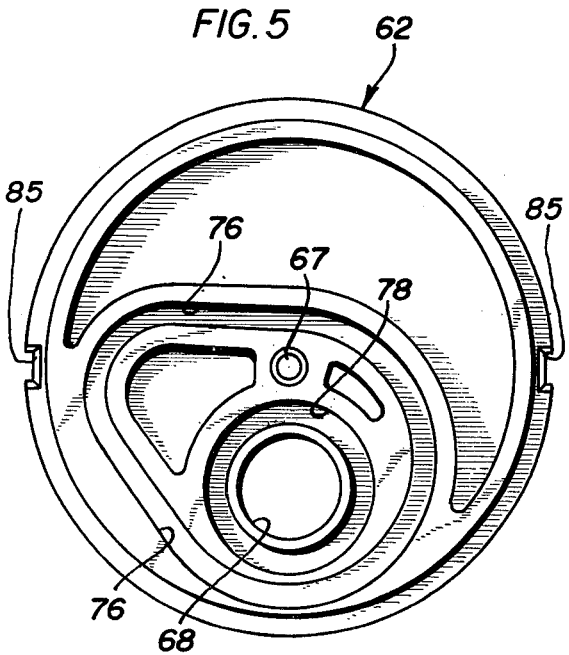

VACUUM CURETTAGE DEVICE

BACKGROUND OF THE INVENTION

The present invention relates to evacuated medical devices, more particularly to an improved, vacuum type of device designed for the performance of a curettage or other similar type of medical procedure.

By way of background, and to place the present invention in proper perspective, it should be noted that evacuated medical devices for performing curettage and other types of medical procedures are known. These devices, like the present device, include an evacuated vessel to which is attached a medical implement, such as a cannula, with some form of valve means being employed to apply the vacuum to said implement.

The prior art designs, to the extent the inventors are aware, employ valve arrangements which have proven difficult to operate effectively in practice; are possessed of a rather short shelf life; and do not utilize means for indicating whether a sufficient vacuum is present. These deficiencies are overcome, to a significant extent, by the present invention.

The medical device of the present invention is not subject to the above-noted disadvantages, and also is possessed of numerous other advantages, as will become apparent from the following description of the drawings and detailed discussion of the illustrated embodiment. In this regard, it should be noted that a preferred form of the present invention will be discussed and illustrated; as such, said discussion and illustration is not intended to define the limits of the invention. In this regard, it is contemplated, and indeed envisioned, that those skilled in the art and possessed of the present disclosure, may devise various alternate structures, or constructions, or devise modifications, which fall within the spirit and scope of the invention, which are defined by the claims appended thereto.

DESCRIPTION OF THE DRAWINGS

Attention is now invited to the drawings, which will be referred to in the detailed discussion of the invention to follow wherein:

FIG. 1 is a perspective view of a medical device constructed in accordance with the present invention;

FIG. 2 is an exploded, perspective view of the medical device of FIG. 1;

FIG. 3 is a partial, longitudinal sectional view taken through the device of FIG. 1;

FIG. 4 is a plan view, illustrating the interior of the cap member of the present invention;

FIG. 5 is a plan view of the upper surface of a manifold member used as part of the valving mechanism of the present invention;

DESCRIPTION OF THE ILLUSTRATED EMBODIMENT

Figure 6:
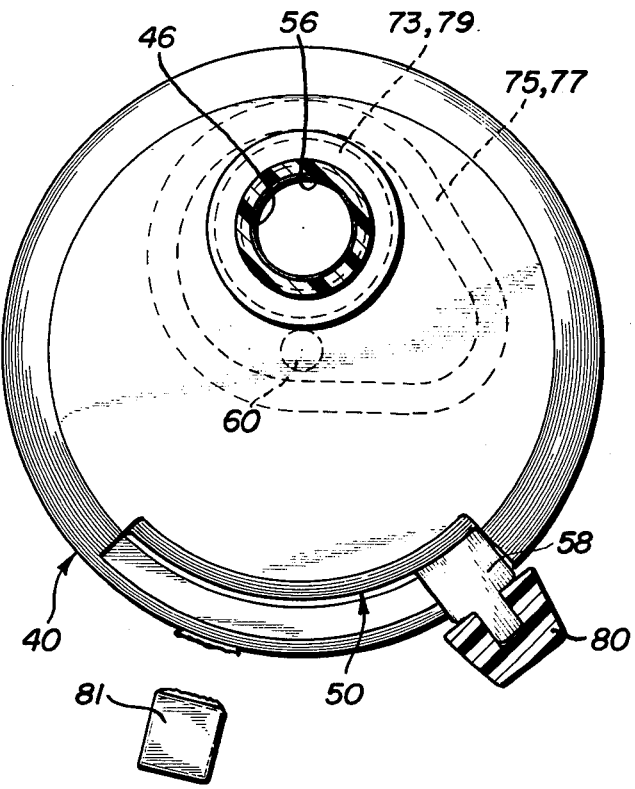
FIGS. 6 and 7 are top plan views of the cover member which illustrate in dotted outline the sealing elements and the valve opening, with FIG. 6 illustrating the valve open condition, and FIG. 7, the valve closed condition.

Attention is initially directed to FIGS. 1 and 2, where there is shown a complete medical device constructed in accordance with the present invention, and designed specifically to be employed in a curettage procedure. FIG. 1 illustrates the device which is designated generally 20, in the assembled condition, while FIG. 2 is an exploded perspective showing the device 20 in the unassembled state.

The medical device 20 of FIGS. 1 and 2 includes a main vessel 22 of a type adapted to be evacuated and withstand the external forces created upon evacuation thereof. The vessel 22 includes a neck portion 24 which provides an opening 26, said neck portion 24 including an external thread 28 to which a combination cover and valve assembly 30 is connected, as is shown in FIG. 1. A medical implement 32, such as a cannula used in performing curettage procedures is connected to the combination cover and valve assembly 30. Thus, upon evacuation of the vessel 22, the vacuum can be applied selectively to the cannula 32 through operation of the valve mechanism, as will be discussed more fully hereinafter.

It should be noted further, that the medical device 20, as illustrated, also includes a vial 34 for the collection of tissue specimens, and an indicator 36 which is designed to provide a visual indication as to the existence of a vacuum within the vessel 22. Both of these elements will be discussed further, after an initial discussion of the valve and cover assembly 30.

The construction of the combination cover and valve assembly 30 is best understood with reference to FIGS. 2 and 3. In this regard, said assembly 30 includes a cover member 40 having a base section 42 and an annular downwardly depending rim 44 which is internally threaded for engagement with the thread 28 on the neck 24 of vessel 22. Cover member 40 also includes an aperture 46 which extends through the base section 42. The upper surface of the cover member 40 includes a relatively short tubular section 48 which is in alignment with the aperture 46 and is adapted to receive the end of the cannula 32, as shown in FIG. 3. The cover member 40 also includes an arcuate, through slot 50 proximate the juncture of the rim 44 and the base section 42. As will become more apparent from the following discussion, the slot 50 accommodates a tab element used on the valve plate, which tab element extends exteriorly of the cover member and provides for manual operation of the valve means.

Discussion will now be had relative to the valving mechanism that is employed with the cover member 40. In this regard, a valve plate 52 having a centrally disposed aperture 54 and a larger, radially offset aperture 56 is assembled within the cover member 40. Valve plate 52 includes a peripheral tab 58 which extends through the slot 50 upon assembly. With reference to FIG. 3, it can be seen that the valve plate 52 is mounted interiorly of the cover, with the central aperture 54 being engaged over a downwardly depending post 60 formed on the undersurface of the base section 42. The engagement of the post 60 and aperture 54 is such that the valve plate 52 is freely rotatable relative to the cover member 40, so that the disposition of the aperture 56 relative to the aperture 46 in said base section can be controlled through manipulation of the tab 58.

In addition to the valve plate 52, a manifold member 62 is also disposed within the cover member 40. The construction of this manifold member 62 is best understood with reference to FIG. 3. Basically, the manifold member 62 is designed to conform to the shape of the cover member 40, and is of sufficient size to overlie the rim of the vessel neck 24, with a gasket 64 being provided therebetween to effect an air tight seal. The manifold member 62 is received within the cover member 40 and engaged against an abutment shoulder 66 formed interiorly of the rim 44, as can be seen from FIG. 3. Said manifold member 62 includes a central recess 67 in which is engaged the end of the post 60 with a force fit to attain assembly of the manifold member within the cover member 40. When this manifold member 62 is assembled as shown in FIG. 3, the valve plate 52 is clamped between said manifold member 62 and the base section 42, however, due to the seating of the manifold 62 on shoulder 66, overclamping of the valve plate 52 is prevented and said valve plate remains freely rotatable.

The manifold member 62 further includes a through aperture 68 which is defined partially by a tubular section 70 extending downwardly from the lower surface portion of said manifold member well into the vessel 22. Assembly of the manifold member 62 of the illustrated embodiment is effected so that the aperture 68 therein is in alignment with the aperture 46 in the base section 42. Of course, if desired, a valve arrangement could be employed wherein alignment of aperture 68 and 46 is not required, merely through use of interconnected internal passages.

As can be seen from FIG. 3, communication between the apertures 68 and 46 is controlled by the valve plate member 52 and the disposition of the aperture 56 with respect to a manifold member 62 and base section 42. As will be discussed more fully with regard to FIGS. 6 and 7, manual operation of the tab 58 can be employed to alter the relative position of aperture 56 in order to achieve interconnection of the respective apertures or passages 68 and 46. The degree of alignment of the aperture 56 with said passages, will effect the rate at which the vacuum is applied to the cannula 32.

The sealing arrangement employed with regard to the valve mechanism will now be considered, which arrangement, not only prevents undesired loss of the vacuum, but also facilitates the rotatable mounting of the valve plate 52 and provides ease of operation thereof. In this regard, with reference to FIG. 4, it can be seen that the interior or lower surface of the base section 42 is provided with two channels 72 and 74. The channel 72 is of a non-circular configuration, and is disposed in outboard relation to the channel 74, the latter of which is generally circular and surrounds the aperture 46. It should be further noted, that the channel 72 also circumscribes the post 60. Disposed in the channels 72 and 74, are a pair of O-rings 73 and 75, which upon assembly of the device, will engage the valve plate member 52. Correspondingly, the upper surface of the manifold member 62, as shown in FIG. 5, includes a pair of similarly shaped and oriented grooves 76 and 78. Groove 78 is circular and surrounds the aperture 68, while the groove 76 is disposed outboard of the groove 78 and is of a shape similar to the aforementioned group 72. A pair of O-rings seals 77 and 79 are disposed in said groove; which O-rings engage the undersurface of the valve plate 52, as shown in FIG. 3.

It will be recalled that the cover member 40 includes a shoulder 66 against which the manifold member 62 is seated, with the valve plate 52 disposed therebetween. Prior to mounting of the valve and cover assembly to the vessel 22, assembly of the manifold member 62 to the cover member 40 is maintained by the friction engagement of said manifold member with the post 60. Since the manifold member 62 is sized to overlie the rim of vessel 22, mounting of the cover member 40 to said vessel will maintain the manifold member 62 and valve plate 52 in proper position, with the manifold member abutted against shoulder 66. The seating of the manifold member 62 on the shoulder 66 serves a number of purposes. Initially, it prevents overlcamping of the valve plate 52, and assures that it can rotate freely. Secondly, the spacing within the cover member 40 is such that when the manifold is seated, the initial sealing contact of the O-rings 73, 75 and 77, 79 with the valve plate 52 is achieved. The sealing contact is such that while the passage of air is precluded, the seals do not tend to impair rotation. If desired, a lubricant may also be employed to further promote free rotation.

As a further point, with the design illustrated, the seals 73, 75 and 77, 79 are positioned in opposed relation. Accordingly, the forces on the valve plate 52 created upon assembly are balanced. This factor is important in that it tends to facilitate the free rotation of the valve plate 52, especially upon initial opening of the valve mechanism, a feature which is important in providing a device that can be controlled with some degree of precision.

With initial reference to FIG. 4, it can be seen that the rim 44 includes a pair of protuberances 83 which are not diametrically opposed. Correspondingly, the manifold member 62 is provided with similarly positioned notches 85. The notch 85 and protuberances 83 are positioned such that the manifold member 62 can only be assembled with the cover with O-ring groove 76 in proper alignment with O-ring groove 75. As a further feature, the engagement of the protuberances 83 in notches 85 preclude undesired rotation of the manifold member 62 with regard to the cover 40, which, if it should occur, could produce misalignment and adversely effect the air tight seal obtained.

Figure 7:
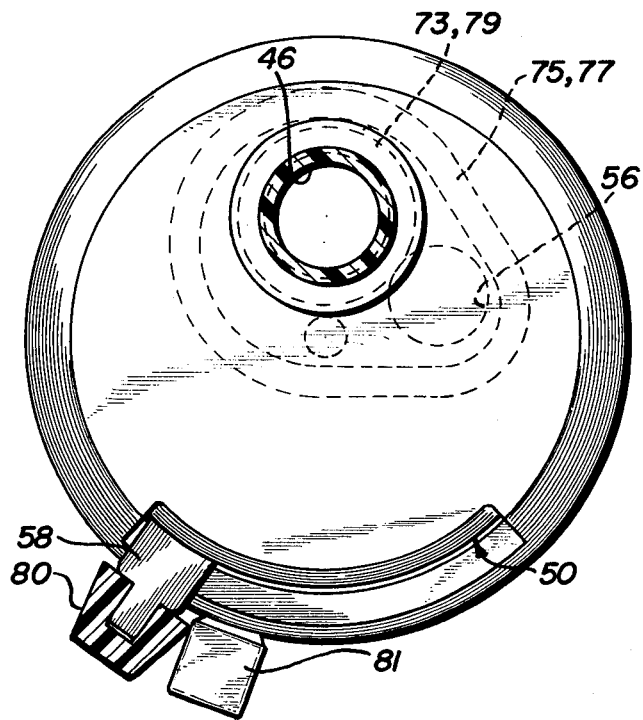

With the above discussion in mind, attention is now invited to FIGS. 6 and 7 which illustrate the relationship of the valve plate member 52 to the sealing arrangement in the open condition, FIG. 6, and in the closed condition, FIG. 7. It should be noted initially, that in FIG. 6 and 7, the sealing members are shown in dotted outline as is the aperture 56. Further, since the respective grooves and seals are of similar shape, seal 75 and 77 are superimposed, as are seals 73 and 79. Looking now to FIG. 7, which is the closed condition, it can be seen that the tab 58 is in the far left hand portion of the slot 50, as viewed, with the aperture 56 out of register with the apertures 46 and 48. The tab 58 may have a knob or the like 80 affixed thereto. In addition, a tamper-proof, break-off tab 81 may be provided, against which the knob 80 will engage upon an attempt to move it in a counter-clockwise direction. Accordingly, the tab 81 prevents inadvertent operation of the valve mechanism, and also provides a visual indication as to tampering of premature operation of the overall assembly.

The overall assembly as discussed lends itself to ease in the assembly process. In this regard, the valve plate 52 sans knob 80 and manifold 62, along with the sealing arrangement, may be assembled to the vessel 22. Accordingly, with said knob 80 removed, the valve can be opened to permit evacuation, and then closed, without damage to the break-off tab 81. Once evacuation is completed, knob 80 is assembled to the tab 58, with the break-off tab 81 preventing inadvertent operation.

An extremely important factor is that in the closed condition of FIG. 7, assuming evacuation of the vessel 22, the opening 56 in the valve plate 52 remains inboard of the seals 75 and 77, thus in the valve closed condition, the seals 75 and 77 prevent leakage of the air along the interface of the valve plate member 52 with the manifold member 62 and the cover member 40. The seal 73 and 79 prevent leakage of air inwardly from the cannula 32 through the opening 56 and the apertures 46 and 68. It should be noted that while it is necessary that both seals 75 and 77 be used in the illustrated embodiment, as a practical matter, the device will function with only one of the seals 73 or 75 employed to seal off the path of air inwardly from the cannula. In this regard, as noted only one seal is required, however, two such seals are preferred in order to obtain the balanced engagement discussed previously.

When it is desired to utilize the device 20, the tamper-proof tab 81 is broken off. Once this is done, it is possible for the user, normally a surgeon engaged in performing a curettage procedure, to rotate the valve plate 52 in a counter-clockwise direction, as viewed. Movement in the counter-clockwise direction will bring the valve plate aperture 56 into some degree of alingment with the apertures 46 and 68 with full alignment being illustrated in FIG. 6. Accordingly, as the aperture 56 is brought into alignment with the opening 46 formed in the cover member and the opening 68 in the manifold member, the vacuum contained within the vessel 22 is applied to the cannula 32.

It is contemplated and intended, that during use the degree of movement of the valve plate 52 will vary from the extremes as illustrated in FIGS. 6 and 7. That is to say, the user or surgeon may apply something less than the entire vacuum to the cannula 32, by bringing only a selected segment of the opening 56 into register with the apertures 46 and 68, and then closing the valve. The degree of alignment determines the rate at which the vacuum is applied and thus affords control in the application thereof. In this regard, it should be noted that during movement of the valve plate 52 from the closed condition of FIG. 7, the opening 56 will at all times remain within the zone defined by the outboard seals 75 and 77. Accordingly, upon initial registry of the apertures 58, 46 and 68, the vacuum within the vessel 22 will be maintained against leakage along the interface of the valve plate with the cover member 40 and the manifold member 62. Thus, during use, the surgeon may control the application of the vacuum to the cannula; viz., that initial steps of the curettage procedure can be performed, a vacuum applied to draw tissue specimens into the vessel 34, the valve then closed to preserve a portion of the vacuum for use in subsequent stages of the curettage procedure. During operation of the valve, the opening 56 will pass over or under the O-ring seals 79 and 73 respectively. To insure against damage to the seals by the rim of opening 56, said rim is coined or otherwise rounded so that it will not tear or cut the O-rings.

With reference to FIG. 1, it will be noted that cannula 32 is hollow and includes an opening 87. This opening has rather sharp edges which are employed in the removal of tissue specimens during curettage procedure. The tissue specimens will be drawn by the vacuum down the hollow cannula interiorly of the vessel 22 wherein they are collected in the specimen via 34. The means provided for mounting the vial 34 to the manifold member 62 will now be considered with reference to FIG. 3.

It should be noted that in addition to the tubular segment 70, the manifold member 62 also includes an annular, downwardly depending flange 82 disposed outboard of said tubular segment 70. The flange 82 is stepped to provide an abutment shoulder 84 and also includes a series of slots 86 formed therein which slots extend to a location disposed above said abutment shoulder 84 and in effect divide the flange 82 into a number of flexible segments, such that said flange 82 is termed resilient. The opening in the specimen vial 34 is sized such that when said vial is engaged over the flange 82, the aforementioned segment of said flange will be flexed inwardly to provide a friction fit with said vial. The vial 34 is moved axially of the flange until the upper edge thereof is engaged with the abutment shoulder 84. Since the slots 86 extend beyond said shoulder 84, the upper portion of said slots 86 remain open and uncovered by said vial 34. These open, upper portions of the slots 86 provide a path for the vacuum from the vessel 22 interiorly of the vial 34. As can be appreciated, since a path is provided for a vacuum interiorly of the vial 34, said vacuum can be applied to the aperture 68 and from there to the cannula 32.

Preferably, the majority of the slots 86 formed in the flange 82 are disposed remote from the tubular segment 70. More specifically, with the majority of the slots 86 disposed remote from the tubular section 70, a rather torturous path is provided for the vacuum. Thus, as the tissue specimens enter the vial 34, they will tend to fall to the bottom thereof, rather than being drawn into the slots 86. As an additional factor, it should be noted that the tube segment 70 is of sufficient length so as to extend below the open portions of the slots 86, thereby further promoting the above-mentioned torturous path for the vacuum and facilitating collection of tissue specimens within the vial 34.

When the vessel 22 is evacuated, the pressure differential created will produce a downwardly force upon the manifold member 62. Should the manifold member bow or flex, the necessary engagement of the sealing arrangement with the valve plate 52 may be destroyed. Accordingly, the under surface of the manifold 62 is provided with a lattice of strengthening ribs 90 and 92 which prevent flexing of the member 62 under any resultant forces produced due to the pressure differential created upon evacuation of the vessel 22.

As was discussed previously, several of the problems encountered with the prior art type of vacuum devices, were loss of vacuum and the inability of the user to determine whether or not a vacuum still existed within the vessel preparatory to use, without actually opening the valve. The present invention not only provides a valving mechanism which prevents loss of vacuum, but there is also disclosed two novel and unique types of vacuum indicators, as will now be discussed with regard to FIGS. 8–13.

Figure 8:
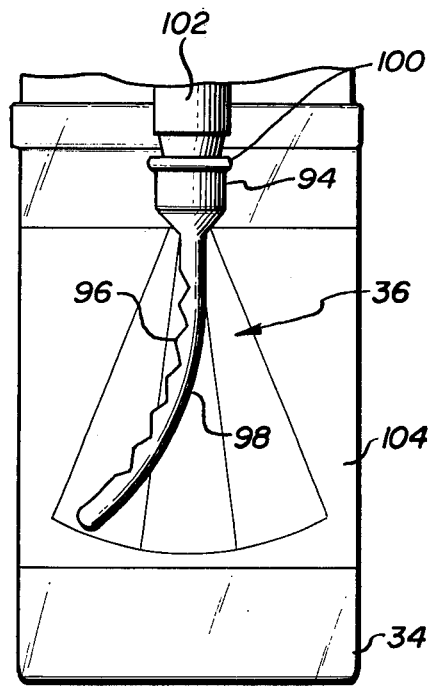
FIG. 8 is a partial, elevational view of one type of vacuum indicator that can be employed with the present invention, in the condition prior to evacuation of the vessel.
Figure 9:
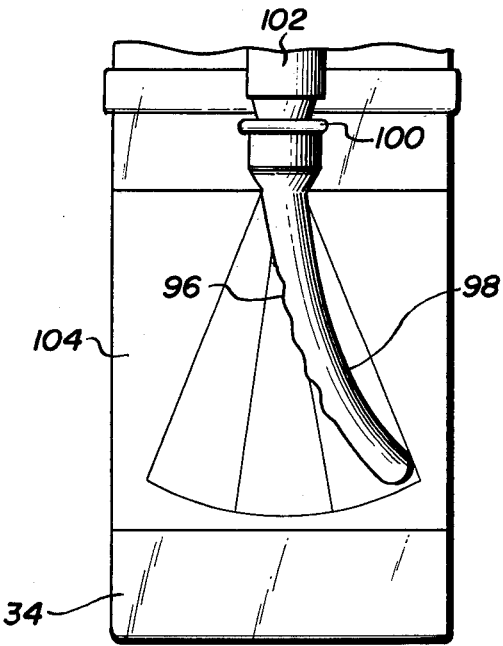
FIG. 9 is a view similar to FIG. 8, but illustrating the condition of the indicator upon evacuation of the vessel.
Figure 10:
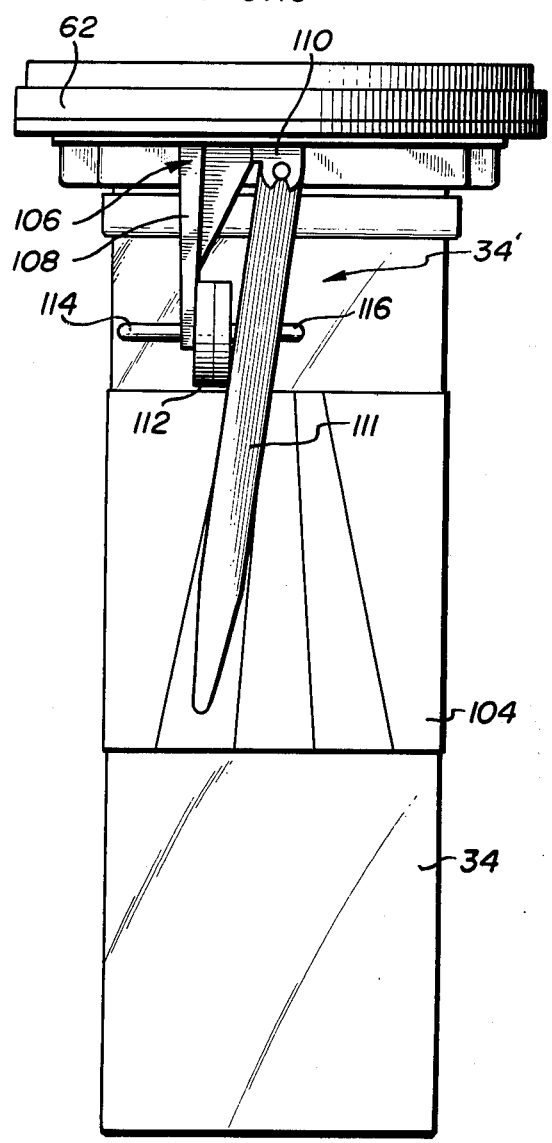
FIG. 10 is a partial plan view of a second type of vacuum indicator, in the pre-evacuation condition.

Attention is first directed to FIGS. 8 and 9, wherein there is illustrated one form of vacuum indicator 34.

The indicator is comprised of a tubular member 94 formed from an elastomeric material, or the like, and having a somewhat elongate cross section, so as to provide a pair of opposed surface portions 96 and 98. As can be seen in FIG. 8, the surface portion 98 is relatively smooth, while surface portion 96 is provided with a plurality of the irregularities in the form of V-shaped ribs. The tubular member 94 is molded, with a closed end and an open end 100, the latter of which is engaged over a post like projection 102 formed on the undersurface of the manifold 62 upon assembly and prior to evacuation. As such, a quantity of air will be trapped within the tubular member 94.

In fabricating the tubular member 94, the relatively smooth surface 98 is formed to have an effective length which is greater than that of the irregular surface 96, when said surface 96 is in the relaxed or unexpanded condition. Accordingly, the tubular member 94 will assume the mode or configuration, as depicted in FIG. 8. It should be noted, however, that the actual length (as opposed to the effective length) of the surface 96 taking into account the irregularities provided by the V-shaped grooves, is greater than that of the smooth surface 98. Accordingly, when the vessel 22 is evacuated, a pressure differential is created due to the air trap within the tubular member 94, which pressure differential will cause tubular member 94 to expand. When this occurs, the irregular surface 96 will tend to straighten out. This will increase the effective length of the surface 96, and the tubular member 94 will assume the position as illustrated in FIG. 9. It will be noted, that the degree of movement of the tubular member 94 from the position as shown in FIG. 8 to that as shown in FIG. 9, will depend upon the degree of evacuation or vacuum achieved.

It is contemplated, that a label 104 may be applied to the vial 34, which label includes indicia or zones calibrated in accordance with precalculated degrees of movement of the tubular member 94 when subjected to a vacuum. Thus, the position of the tubular member 94 relative to said label will provide a visual indication as to the degree of vacuum present within the vessel 22.

Figure 11:
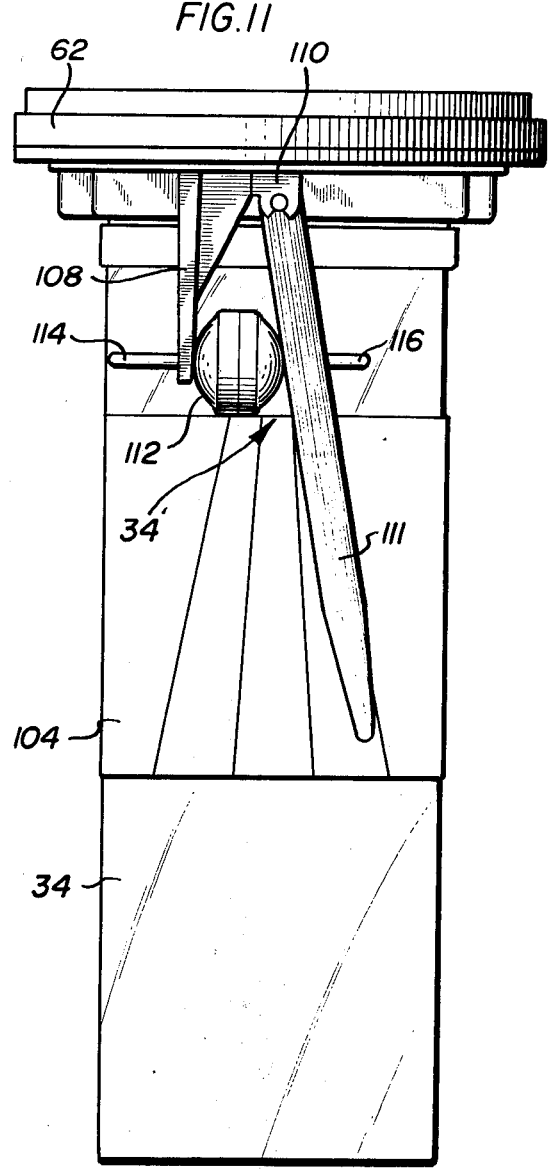
FIG. 11 is a view similar to FIG. 10, but illustrating the condition of the indicator upon evacuation of the vessel.
Figure 12:
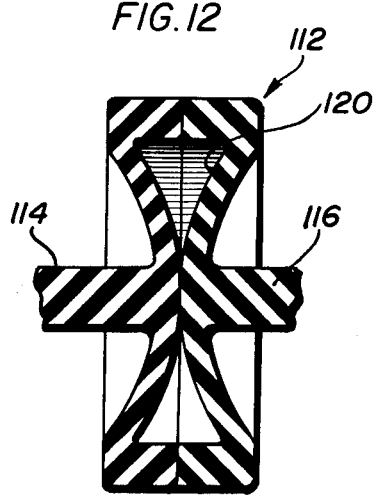
FIGS. 12 and 13 are sectional views taken through the indicators of FIGS. 10 and 11, respectively.

In FIGS. 10-13, an alternate yet preferred type of vacuum indicator 34' is illustrated. Basically, the indicator 34' includes a base section 106 which is secured to the manifold member 62. Said base section 106 includes a downwardly depending segment 108. The base section 106 also includes a bracket 110 which is formed as an integral part thereof. An elongate pointer or indicator 111 is pivotally connected to the bracket 110, and extends downwardly from the manifold member 62 as shown. A bellows member 112 is provided, which includes oppositely disposed post like extensions or sections 114 and 116, one of each being connected to the segment 108 and the pointer 111, as shown. With reference to FIG. 12, it can be seen that the bellows member 112 is of a hollow construction and defines an interior or plenum chamber 120.

Figure 13:
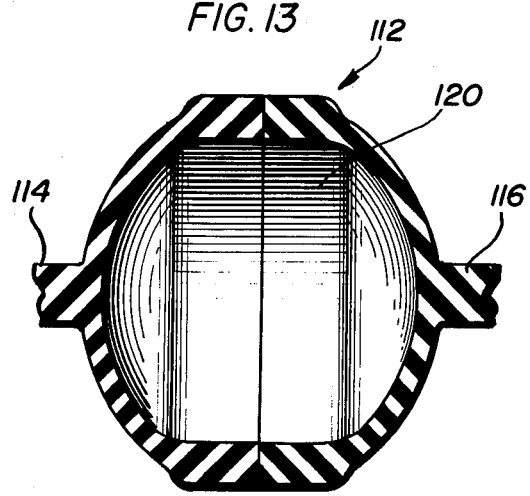

The bellows member 112 is fabricated or assembled under atmospheric conditions, so that a quantity of air is trapped within the chamber 120. Accordingly, assuming assembly of the indicator 34' within a vessel and subsequent evacuation thereof, the bellows 112 will expand, assuming a condition similar to that as indicated in FIG. 13. With reference to FIG. 11, it will be noted that the segment 108 to which the post 114 is connected is stationary, thus all of the movement of the bellows upon expansion thereof will be translated to the elongate pointer or indicator 111, which it will be recalled is pivotally mounted. Thus, the degree of expansion of the bellows can be precalculated and employed in the movement of the indicator 111 to provide a visual indication as to the presence of a vacuum within the vessel 22 or the degree of vacuum present therein, similar to the indicator as discussed relative to FIGS. 8 and 9.

Both the tubular member 94 and the bellows 112 of the vacuum indicator discussed above, are designed to hold only a very small, predetermined quantity or volume of ambient air. Thus, upon evacuation of the vessel 22, and expansion of the respective members 94 and 112, a overly low pressure level will exist. If too much air is trapped within the members 94 and 112, expansion may be excessive upon evacuation and could lead to a malfunction of the indicators. As an additional factor, with reference to FIG. 3, the mounting flange 82 for the vial 34 has been purposely offset with respect to the central axis of the manifold member 62. This then allows sufficient room for assembly of the vacuum indicators 34 or 34' to the manifold, while enabling the entire assembly to pass interiorly of the vessel 22. Also, the mounting for the vial 34 has been selected to provide for rotation of said vial. Thus during assembly of the vacuum indicator 34 or 34', the vial can easily be rotated to align the indicator with the proper indicia on the label 104 indicating ambient or atmospheric pressure.

There has been illustrated and disclosed an improved, evacuated medical device of a preferred design. While others may devise various modifications and variations from the disclosed structure, these may well fall within the spirit and scope of the invention, which are defined by the claims appended hereto.

The invention is claimed as follows:

1. An indicator for providing a visual indication as to the presence of a vacuum within a sealed vessel, or the like, said indicator including a tubular element having an open end and a closed end, said tubular element having a cross-section which defines first and second oppositely disposed exterior surfaces, said first surface being substantially smooth, said second of an irregular configuration, said first surface having an effective length, in the relaxed condition, which is greater than the effective length of said second surface in the relaxed condition, the actual length of said second surface, taking into account the irregularities formed therein being greater than that of said first surface, such that said tubular element may be assembled to a post or the like, positioned interiorly of a vessel to be evacuated by engagement of said open end over said post to trap a quantity of air within said element, said tubular element assuming a first orientation when in the relaxed condition, such that upon the creation of a vacuum within a vessel, the air trapped within the tubular element will tend to expand said element such that the differences in the acutal length of said first and second surfaces will produce movement of the element to a second orientation indicating the presence of a vacuum within the said vessel, with the degree of movement depending upon the level of the evacuation existing in the vessel.

2. An indicator as defined in claim 1, wherein said irregularities are in the form of V-shaped grooves formed in said second surface.

3. A medical device such as a curette or the like, including a vessel adapted to be evacuated, and valve means for selectively applying said vacuum to a medical implement attached to said device, such as a cannular or the like, said valve means being housed within a combination cover means and valve means assembly for said vessel, which assembly comprises; a generally cup-shaped cover member adapted for connection to said vessel and including a base section having an opening formed therein; a manifold member also having an opening formed therein and being disposed interiorly of said cover member; a relatively movable valve plate disposed between said cover member and said manifold member, and including an aperture adapted to be brought into registration with said base section opening, said valve plate being movable between two limits, the first defining a valve closed position, and the second a valve fully opened positioned; sealing means for preventing the loss of vacuum from said vessel when said valve plate is in said valve closed position, and providing for application of said vacuum to said cover member opening during movement of said valve plate to said second position; said manifold member including inwardly directed flange means formed on said manifold member in surrounding relation to said opening in said manifold member; and vial means engageable over said flange means and adapted for the collection of tissue specimens; said flange means including means providing at least one opening above the upper edge of said vial means so that the vacuum in the vessel can be applied to said manifold member opening, and upon the operation of said valve means said vacuum can be applied to said cover member opening.

4. A medical device according to claim 3 wherein said means providing at least one opening above the upper edge of said vial comprise one or more elongate apertures formed in said flange means, and said flange means further including downwardly facing stop means against which the upper edge of said vial is abutted upon engagement over said flange means, said elongate aperture means extending to a location above said stop means such that at least a portion of said elongate aperture means remain open to provide a path for the application of a vacuum from said vessel to said manifold member opening when said vial is so engaged over said flange means.

5. A medical device according to claim 4, wherein said elongate aperture means comprises a slots extending from the rim of said flange means to said location, which slots provide said flange means with a degree of resiliency, thereby enabling the specimen vial to be attached thereto with a friction fit.

6. A medical device according to claim 4, wherein said elongate aperture means are provided by a plurality of slots formed in said flange means, with a number of said slots being displaced from said opening in said manifold member to reduce the possibility of clogging of said slots with tissue specimens.

7. A medical device according to claim 4, wherein said manifold member includes an elongate, tube like section extending downwardly from said lower surface portion in alignment with the opening in the said manifold member, said tube like portion extending to a location below said abutment means so as to provide a circuitous path from the interior of said vessel to said opening in the manifold member thereby to reduce the possibility of tissue specimens clogging said openings during operation of said medical device.

8. A medical device according to claim 3, wherein said cover member includes an arcuate slot and said valve plate includes a tab extending through said slot to provide for manual operation of said valve plate.

9. A medical device such as a curette or the like, including a vessel adapted to be evacuated, and valve means for selectively applying said vacuum to a medical implement attached to said device, such as a cannular or the like, said valve means being housed within a combination cover means and valve means assembly for said vessel, which assembly comprises; a generally cup-shaped cover member adapted for connection to said vessel and including a base section having an opening formed therein; a manifold member also having an opening formed therein and being disposed interiorly of said cover member; a relatively movable valve plate disposed between said cover member and said manifold member, and including an aperture adapted to be brought into registration with said base section opening, said valve plate being movable between two limits, the first defining a valve closed position, and the second a valve fully opened position; sealing means for preventing the loss of vacuum from said vessel when said valve plate is in said valve closed position, and providing for application of said vacuum to said cover member opening during movement of said valve plate to said second position; a vacuum indicator carried by said manifold member, interiorly of said vessel, said vacuum indicator including means responsive to pressure differences to provide a visual indication as to the presence of a vacuum in said vessel.

10. A medical device according to claim 9, wherein said vacuum indicator includes a tubular element formed from elastomeric material, or the like, said tubular element having a cross section which defines two opposed exterior surfaces, one said surface being substantially smooth, while the other is of an irregular configuration and of a greater surface area than said one surface, but is of lesser effective length when said tubular element is in a relaxed condition, than said smooth surface, said tubular element being affixed to said manifold member under atmospheric condition such that a volume of air will be trapped therein, with said tubular element assuming a first orientation, such that upon the creation of a vacuum within said vessel, the air trapped within the tubular element will tend to expand said element such that the differences in the actual area of said respective surfaces will produce movement of the element to a second orientation indicating the presence of a vacuum within the said vessel, with the degree of movement depending upon the level of the evacuation existing in the vessel.

11. A medical device according to claim 10, wherein said tubular element includes an open end and a closed end, said open end being engaged over a post member formed on the lower surface of said manifold member to trap a volume of air within said tubular element.

12. A medical device, such as a curette or the like, comprising; a vessel adapted to be evacuated and having an opening therein; a combination cover and valve means assembly engaged with said vessel in covering relation to said opening, such that through operation of said valve means a vacuum may be applied to a medical implement connected to said device, said assembly, including a cover member having an opening therein and means for attaching a medical implement to said cover member, and a valve plate rotatably carried within said cover member for movement in a plane from a valve closed position to a valve open position, said valve plate including an aperture formed therein which may be selectively aligned with that formed in said cover member in the valve open position, said valve plate including a tab extending through a slot formed in said cover member to provide for manual operation thereof, and a knob member engageable with said tab, said cover member including a frangible element formed integral therewith proximate an end of the slot occupied by said tab in the valve closed position, said frangible element being positioned with respect to said slot such that when said knob member is so engaged said valve plate cannot be rotated to the valve open position, without first removing said frangible element, however, when said knob is removed, said valve plate may be rotated to the valve open position to evacuate said vessel, without interference from said frangible element.

* * * * *